United States Patent [19]

Herbst

[11] Patent Number: 5,545,173
[45] Date of Patent: Aug. 13, 1996

[54] APPARATUS FOR TAKING BLOOD SAMPLES

[76] Inventor: Richard Herbst, Freisinger Strasse 3 b, D-85386 Eching, Germany

[21] Appl. No.: 252,111

[22] Filed: Jun. 1, 1994

[30] Foreign Application Priority Data

Jun. 2, 1993 [DE] Germany .............. 43 18 142.2

[51] Int. Cl.⁶ .................................................. A61B 5/14
[52] U.S. Cl. .................................................. 606/181
[58] Field of Search ............... 128/749, 751–754; 606/181–183

[56] References Cited

U.S. PATENT DOCUMENTS

| 4,676,244 | 6/1987 | Enstrom . |
| 4,712,548 | 12/1987 | Enstrom . |
| 4,738,261 | 4/1988 | Enstrom . |

FOREIGN PATENT DOCUMENTS

| 0255338 | 2/1988 | European Pat. Off. . |
| 0403873 | 12/1990 | European Pat. Off. . |
| 0427406 | 5/1991 | European Pat. Off. . |
| 3111737 | 2/1982 | Germany . |
| 9205278 | 6/1992 | Germany . |
| WO9108712 | 6/1991 | WIPO . |
| WO9219164 | 11/1992 | WIPO . |

*Primary Examiner*—Max Hindenburg
*Attorney, Agent, or Firm*—Knobbe, Martens, Olson & Bear

[57] ABSTRACT

The disclosed apparatus comprises an elongate lancet portion and an elongate sleeve portion for receiving and axially guiding the lancet portion. The lancet portion has a knob section on one end thereof and protruding lancet cutting edge section on the other end thereof. The lancet portion is held in the sleeve portion via a preset breaking point. In a first operational position the protruding lancet cutting edge section is entirely enclosed within the sleeve portion. Upon exertion of a predetermined amount of axial force between the lancet portion and the sleeve portion the preset breaking point is broken and a transition occurs in the relative position between the lancet portion and the sleeve portion to make the lancet cutting edge section protrude from the sleeve portion, thus cutting into a patient's skin and causing blood to exit therefrom.

16 Claims, 5 Drawing Sheets

APPARATUS FOR TAKING BLOOD SAMPLES

BACKGROUND OF THE INVENTION

1. Field of the Invention

The present invention relates generally to an apparatus for taking blood samples, and more specifically, to such apparatus comprising:

an elongate lancet portion defining an axis and having a first and second terminal end, the first lancet portion terminal end being provided with a knob section and the second lancet portion terminal end being provided with a protruding lancet cutting edge section;

an elongate sleeve portion for receiving and axially guiding the lancet portion, the sleeve portion having a first and a second terminal end, the first sleeve portion terminal end being provided with a flange; and a mechanical axial obstacle arranged between the lancet portion and the sleeve portion, the mechanical axial obstacle being adapted to the overcome upon application of a predetermined amount of axial force between the lancet portion and the sleeve portion, wherein the lancet portion, in a first operational position, is axially held within the sleeve portion with the knob section being at a first axial distance from the flange and the protruding lancet cutting edge section being entirely enclosed by the second sleeve portion terminal end, whereas, in a second operational position, the lancet portion is axially held within the sleeve portion with said knob section being at a second axial distance from the flange and the protruding lancet cutting edge section protruding from the second sleeve portion terminal end, the mechanical axial obstacle acting as an axial stop between the lancet portion and the sleeve portion, whereas upon application of the predetermined amount of axial force between the lancet portion and the sleeve portion the mechanical axial obstacle is overcome, resulting in an abrupt transition from the first to the second operational position.

2. Brief Description of the Prior Art

An apparatus of the afore-mentioned kind has been known from U.S. Pat. No. specifications 4,676,244 and 4,712,548 and 4,738,261.

This prior art apparatus for taking blood samples has a sleeve portion being provided with a through bore. An axial stop extends radially into the through bore. The lancet portion, in contrast, is provided with a peripheral bulge such that the lancet portion, in the first operational position, rests on the axial stop.

If the lancet portion and the sleeve portion are axially pressed together, then the mechanical resistance as established by the annular bulge of the lancet portion and resting on the radial stop within the through bore of the sleeve portion is overcome. The axial force exerted on the lancet portion is, thus, abruptly set free so that the lancet portion, having previously been entirely enclosed within the sleeve portion, now suddenly shoots to the opposite end of the sleeve portion. If the apparatus is applied, e.g. on the finger tip of a patient, the lancet portion will intrude into the finger tip and patient blood will exit therefrom. The blood may then be taken for a subsequent medical laboratory examination.

The prior art apparatus is manufactured in an injection molding machine tool as one piece. For that purpose the design is such that the lancet portion is molded to annular flange of the sleeve portion such that the lancet cutting edge section extends into the annular flange of the sleeve portion and is, hence, embedded in the annular flange plastic material. In such a way the lancet cutting edge section is kept sterile prior to the use of the blood taking apparatus because it is entirely surrounded by plastic material.

When a blood sample is to be taken, one has, therefore, to first manually separate the lancet portion from the sleeve portion and to then draw the lancet cutting edge section out of the annular flange. The lancet portion must then be fitted into the sleeve portion by inserting a circular cylindrical section of the lancet portion into the through bore of the sleeve portion until the annular bulge, mentioned above, rests on the axial stop.

Blood sample taking apparatuses of the afore-mentioned kind are frequently used by patients themselves, i.e. by medical laymen, for example by patients suffering from diabetes who have to carry out blood controls at their home in regular time intervals. With this kind of people one cannot always be sure that the required manipulations are made with the necessary precision and care.

Therefore, the prior art apparatus has some essential drawbacks.

First of all, the prior art apparatus has the disadvantage that the axial stop to be overcome has the shape of an annular bulge together with a radial stop so that the through bore outside of the radial stop area has a larger diameter, namely the diameter of the annular bulge. Therefore, the lancet portion cannot be exactly, i.e. linearly, be guided within the sleeve portion.

Another disadvantage of the prior art apparatus is that it is designed for one intrusion depth of the lancet cutting edge section only. However, for different patients the skin thickness in the area where the blood sample shall be taken, may be different, too, so that if the intrusion depth is set as a fixed value, this might result in a substantial injury for a patient having a relatively thin skin whereas for other patients having a relatively thick skin the intrusion depth might be unsufficient.

Moreover, the prior art apparatus has the disadvantage that its manipulation requires a certain skill, in particular during the preparation of the apparatus when the lancet portion is to be separated from the sleeve portion and the two portions have to be assembled together. During such manipulations it might happen that inadvertently the lancet portion falls down and the lancet cutting edge section will be contaminated. Further, it cannot be excluded that the patient will be injured during the assembling of the two portions together when the lancet cutting edge section is uncautiously handled. Moreover, it is a certain disadvantage that the patient during the assembling of the two portions together visually becomes aware of the lancet cutting edge section which might have disadvantageous psychological effects.

It is, therefore, an object underlying the invention to improve a blood sample taking apparatus of the kind mentioned at the outset such that the afore-mentioned disadvantages are overcome. In particular, the apparatus shall be improved such that the two portions may be exactly guided on each other. Further, it shall be possible to exactly preset the lancet cutting edge section intrusion depth at selected values. Moreover, difficult manipulations of the apparatus prior to its actual use shall be avoided. Moreover, any contamination of the lancet cutting edge section shall be made impossible and psychological drawbacks with respect to the patient shall be avoided.

SUMMARY OF THE PRESENT INVENTION

Briefly, according to a first embodiment of the invention the apparatus shall be provided with a preset breaking point acting between the lancet portion and the sleeve portion, with the preset breaking point acting as an axial stop between the lancet portion and the sleeve portion in the first operational position whereas upon application of the predetermined amount of axial force the preset breaking point is broken, resulting in the abrupt transition from the first to the second operational position.

According to a second embodiment of the invention, the lancet cutting edge section intrusion depth may be preselected and preset by using at least two spacers arranged between the lancet portion and the sleeve portion for establishing either a first or a second, or more axial distances therebetween. Thus, the impact on the shooting movement of the lancet cutting edge section and/or the intrusion depth into the patient's skin may be exactly preset in various different steps, thus making it possible to adapt the apparatus to different patients having different skin properties.

According to a third embodiment of the invention a protection element is arranged on the lancet portion enclosing the protruding lancet cutting edge section. The protection element may be manually removed from the lancet portion to expose the protruding lancet cutting edge section. However, in the first operational position, the protection element is partially enclosed within the sleeve portion to make it possible to grasp the protection element with one's fingers and to remove same. Even after the protection element is removed from the lancet cutting edge section, the section is still enclosed within the sleeve portion and can, therefore, not be seen by the patient when the apparatus is applied to the skin surface.

The measure to design the mechanical obstacle to be overcome as a preset breaking point has the advantage that the guiding function and the mechanical stop function may be separated from each other. In this way the exact guiding of the lancet portion within the sleeve portion is not affected. One can, therefore, as the case may be in a specific application, set the force that is required to mechanically overcome the stop even extremely high without affecting the guiding properties of the sleeve portion with respect to the lancet portion.

The measure to provide at least two spacers establishing two distinct distances in the second operational position has the advantage that with simple design means different intrusion depths of the lanced cutting edge section may be preset according to the patient's skin depth.

The measure to provide a protection element as a section being essentially surrounded by the sleeve portion prior to the taking of a blood sample has, on the one hand side, the advantage that the patient will optically not become aware of the lancet cutting edge section before the blood sample has been taken. On the other hand side we have the advantage that the lancet cutting edge section remains protected within the sleeve portion until the axial taking of a blood sample and can, therefore, not be contaminated. In particular, a separation of the two portions from each other and a fitting of the two portions into each other is not necessary, as compared with the prior art, because the lancet portion and the sleeve portion are already preassembled in their operational position and all that remains to be done is to withdraw the protection element from the sleeve portion in order to make the apparatus ready for use.

According to a preferred embodiment of the invention, the preset breaking point is designed as a perforatable bottom section on the sleeve portion or the lancet portion, respectively, a pin being provided on the lancet portion or the sleeve portion, respectively, the pin registering with the bottom section and punching through the bottom section during the transition.

This measure has the advantage that by properly dimensioning the perforatable bottom section, the axial force for overcoming the stop may be preset in a wide range.

According to a variant of this embodiment the breaking point is designed as a web or as a nose on the sleeve portion or the lancet portion, respectively, a protrusion being provided on the lancet portion or the sleeve portion, respectively, the protrusion registering with the web or nose and shearing off the web or nose during the transition. It goes without saying that, moreover, also other elements that may be sheared off or broken off or teared off or the like may be used as the preset breaking point.

According to another embodiment of the invention the at least two spacers are designed to establish different axial distances between the sleeve portion and the lancet portion also in the first operational position.

This measure has the advantage that the distance between the first and the second operational position and, hence, the impact of movement with which the lancet cutting edge section shoots from the sleeve portion, may be preset. On can, thus, adapt the apparatus to a softer or a harder skin of a patient.

According to a preferred embodiment of the invention the spacer means are designed as axial pins.

This measure has the advantage that a particular simple design is possible and that the various parts of the apparatus may be simple manufactured, e.g. by means of an injection molding apparatus.

In this case it is particularly preferred to make the pins during the transition run in a bore, at least one of the pins being provided with a bulged section having a larger diameter than said bore.

This measure has the advantage that an additional guiding of the lancet portion on the sleeve portion takes place because the pin will run in the afore-mentioned bore. Moreover, a particularly simple design of the stop is obtained as required for defining two distinct distances because the pins may be provided with bulged sections of different axial lengths in a wide range. In this manner by providing an appropriate number of pins two or three or even more different intrusion depths are possible with one and the same blood sample taking apparatus.

According to another improvement of this embodiment, the pins are provided on the knob portion, the flange having throughs registering with the pins.

This measure has the advantage that the distinct positions, i.e. registerings of several pins with respect to the one bore may be set by simply rotating the lancet portion relative to the sleeve portion. By providing appropriate stops or elastic locks in a circumferential direction, these positions of rotation may be appropriately mechanically secured and may, further, be indicated by appropriate optical marks.

With these embodiments it is, further, preferred when the pins have a different axial length.

This measure has the advantage that the different distances may be set in an extremely simple contructive manner.

This measure combines the already mentioned advantages of the pins serving as spacers on the one hand side and with the perforatable bottom section on the other hand side. The perforatable bottom section in this case is preferably arranged at the bottom of a blind bore within the annular flange.

According to other embodiments of the invention the lancet portion comprises a first cylindrical section, as know per se in which a shank portion of the lancet portion is held, moreover, the protection element is designed as a second cylindrical section being essentially flush with the first section.

This measure has the advantage that the lancet portion as a hole, i.e. together with the protection element, may be inserted into the sleeve portion resulting in the lancet cutting edge section to be permanently protected, while the protection element may be separated from the lancet section in an easy manner. If during the time prior to the use of the apparatus contaminations will collect within the chamber of the through bore, then the contamination of the cutting edge section is securely avoided due to the fact that two sections are flush with each other because the protection element is removed only immediately prior to the use of the apparatus.

Insofar it is particularly preferred to provide at least one of the two sections with a tip, the tip forming the transition to the respective other section.

This measure has the advantage that the material bridge between the two sections may be made very small so that on the one hand side, the lancet cutting edge section is enclosed in a sterile manner whereas on the other hand side the protection element may be separated from the lancet cutting edge section with only minimum force.

With all these embodiments it is particularly preferred when all of the elements, except the lancet, are made of a plastic material.

Moreover, it is preferred in these embodiments when the sleeve portion and the lancet portion are manufactured as tightly fitting in each other or an arrangement is selected using a barb.

These measures have the advantage that the two portions are tightly connected to each other when fitted into each other so that none of the portions may inadvertently become lost.

Further advantages will become apparent from the description and the enclosed drawings.

It goes without saying that the afore-mentioned features and the features that will be described hereinafter may not only be used in the combination as explicitly mentioned but may also be used in other combinations or alone, without departing from the scope of the present invention.

Preferred embodiments of the invention are shown in the drawings, and will be described in more detail in the following description.

DETAILED DESCRIPTION OF THE PREFERRED EMBODIMENTS

In FIGS. 1 to 4 reference numeral 10 as a whole, indicates a blood sample taking apparatus appropriate to be used by patients themselves. The blood sample taking apparatus 10 is intended to take blood samples from an appropriate member of the patient's body, in particular from a finger tip. The apparatus is intended to be used for taking blood samples where the taking of a few drops of blood is sufficient.

Figures 1A, 1B:
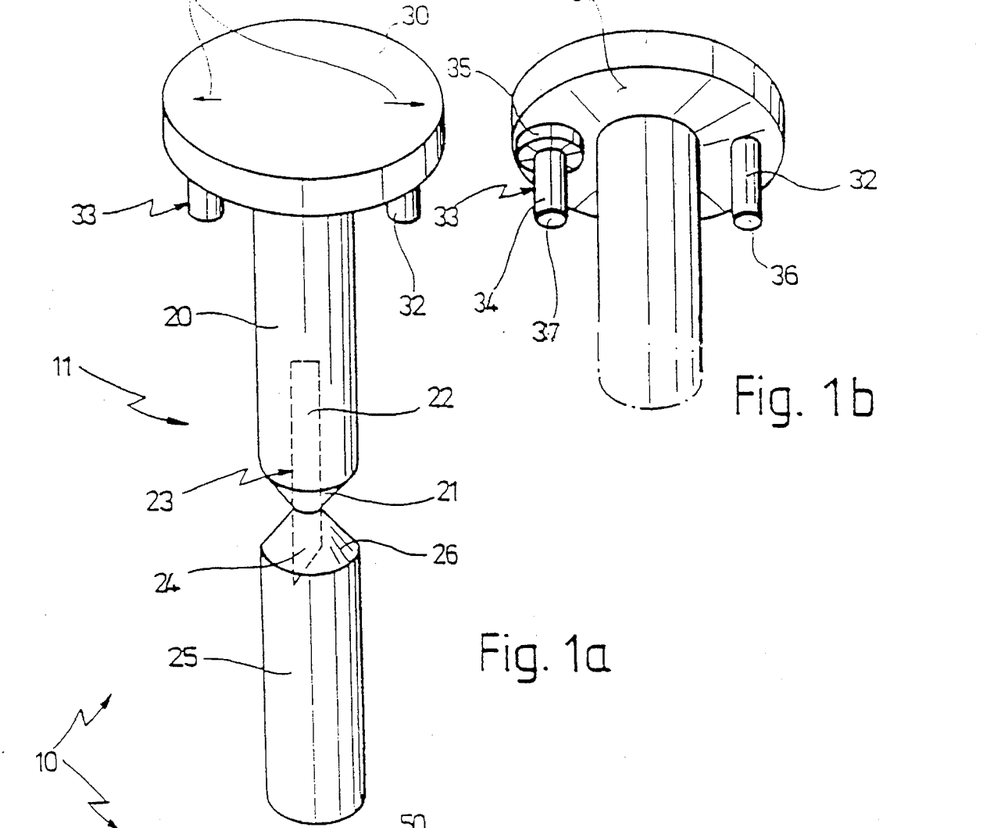
FIGS. 1a and 1b are prospective views, as viewed from above and from below, respectively, under an accute angle (FIG. 1b of the apparatus), of a lancet portion of a preferred embodiment of a blood sample taking apparatus according to the invention.
Figure 2:
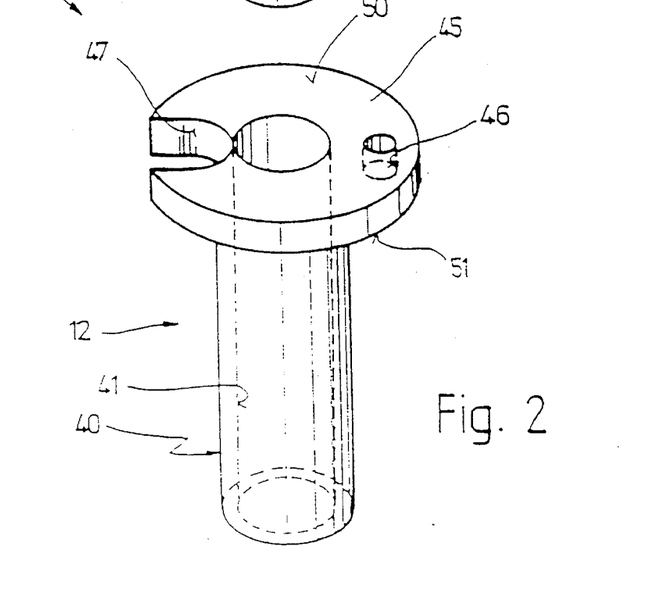
FIG. 2 is an illustration, similar to that of FIG. 1a and depicting a prospective view of an appropriate sleeve portion.

The blood sample taking apparatus 10 comprises a lancet portion 11 and a sleeve portion 12.

Lancet portion 11 is provided with a first cylindrical section 20 terminating downwardly in FIG. 1a in a conical tip 21. First section 20 encloses a shank section 22 of a lancet 23. Lancet 23 has a cutting edge section 24 protruding thus from first section 20. A second cylindrical section 25 of lancet portion 11 encloses cutting edge section 24. Second section 25 terminates upwardly in the illustration of FIG. 1 into a conical tip 26, too.

When lancet portion 11 is integrally manufactured from plastic material by injection molding, only a very thin bridge of plastic material will remain in the transitional area between tips 21 and 26 enclosing cutting edge section 24 of lancet 23.

Figure 4A:
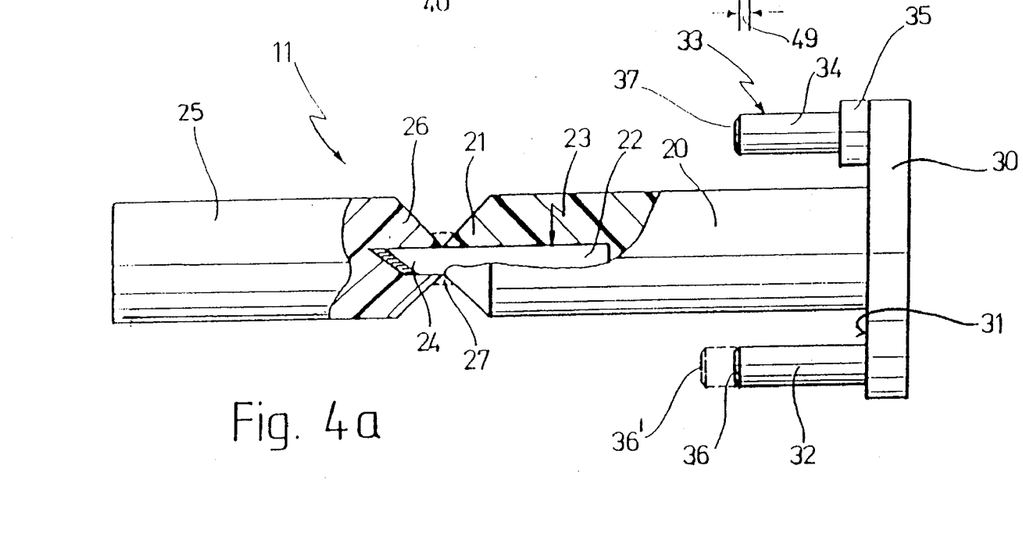
FIGS. 4a and 4b are illustrations, similar to those of FIGS. 3a and 3b, of a lancet portion according to FIGS. 1a and 1b.
Figure 4B:
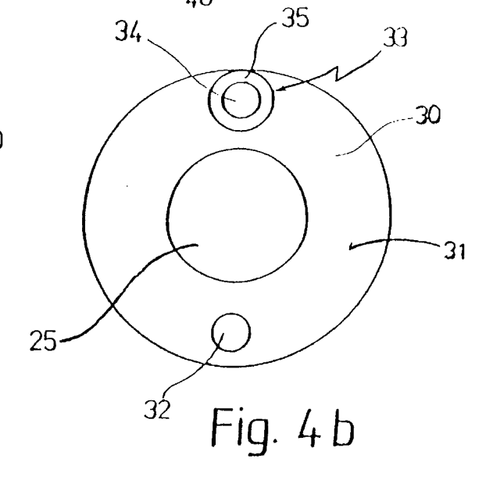

As shown in FIG. 4a one can, however, also provide a cylindrical transition 27 in this area (shown in dashed lines and not in a real scale), for guaranteeing the sterile embedding of lancet 23. An elastic barb 28 (cf. FIG. 5) may be provided at the free end of second cylindrical section 25 for avoiding that lancet portion 11 after insertion into sleeve portion 12 becomes inadvertently lost.

A knob portion 30 is molded to the upper end of first section 20 in FIG. 1a, knob portion 30 being also designed cylindrically but being substantially shorter in an axial direction and having a substantially larger diameter as compared with sections 20 and 25.

A first pin 32 and a second pin 33 being spaced from each other by 180 degrees in a peripheral direction are molded on the same periphery to a bottom side 31 of knob portion 30 in the depicted embodiment. It goes without saying that, as the case may be, also three or four or even more pins of this kind may be provided there.

Whereas first pin 32 has an axially uniform thin design, second pin 33 is provided with two axial sections, namely a lower thinner section 34 and an upper bulged section 35. Pins 32, 33 may be provided with a tip 36 or 37, respectively at their free end, for example may be provided with a small taper.

FIG. 1a, further, shows that on the opposite side of knob portion 30 marks 38 may be provided at the positions of pins 32 and 33, as will be explained below in further detail.

Sleeve portion 12 comprises a hollow-cylindrical section 40. A through bore 41 extends axially through hollow-cylindrical section 40. The inner diameter of through bore 41 corresponds to the same outer diameter of cylindrical sections 20 and 25 with the arrangement being preferably made such that the inner diameter of through bore 41 is a little smaller for establishing a tightly frictional fit between sections 20 and 25 of lancet portion 11 and through bore 41 of sleeve portion 12, provided that there is no barb 28 as described above.

Figure 6:
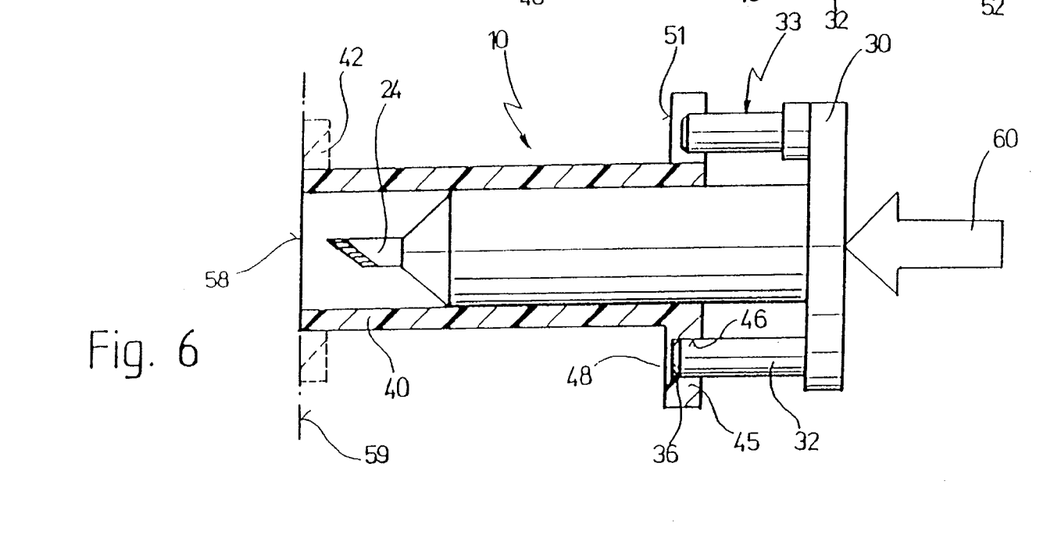
FIG. 6 is an illustration, similar to that of FIG. 5, however, in a first operational position of the apparatus.

As shown in FIG. 6, hollow-cylindrical section 40 may at its left hand terminal end be provided with an application flange 42 in order to increase the application surface of the blood sample taking apparatus 10 on the patient.

Hollow-cylindrical section 40, further, is provided with an annular flange 45 at its upper terminal end in FIG. 2, annular flange 45 being axially substantial shorter, however, being substantially larger in diameter as compared to hollow-cylindrical section 40. The outer diameters of annular flange 45 may, for example, correspond to those of knob portion 30.

Annular flange 45 is provided with a blind bore 46 at one peripheral position and, at another peripheral position spaced by 180 degrees in a peripheral direction, is provided with a cutout 47. Cutout 47 is dimensioned larger than bulged section 35 of second pin 33. Blind bore 46 at its bottom is provided with a thin bottom section 48, as becomes apparent in particular from FIG. 3a. The thickness 49 of bottom section 48 is set depending on the intended perforation force and the stability of the material from which annular flange 45 is made, as will be explained below in further detail.

Annular flange 45 has a top side 50 and a bottom side 51.

As already mentioned before, lancet portion 11 and sleeve portion 12 preferably entirely consist of a plastic material, except for lancet 23. For this purpose lancet portion 11 and sleeve portion 12 are manufactured in a plastic material injection molding machine tool. For that purpose an injection molding tool is used in which lancet portion 11 and sleeve portion 12 are manufactured adjacent to each other during one and the same injection step. During the manufacture of lancet portion 11 lancet 23 is simultaneously embedded by plastic material as becomes particularly apparent from FIG. 4a.

When ejecting portions 11, 12, i.e. removing portions 11, 12 from the injection molding tool, portions 11 and 12 are synchronously unloaded from the injection tool by means of an appropriate handling apparatus (not shown) and are, during the same procedural step, inserted into each other by inserting lancet portion 11 with cylindrical sections 20 and 25 into through bore 41 of sleeve portion.

Figure 5:
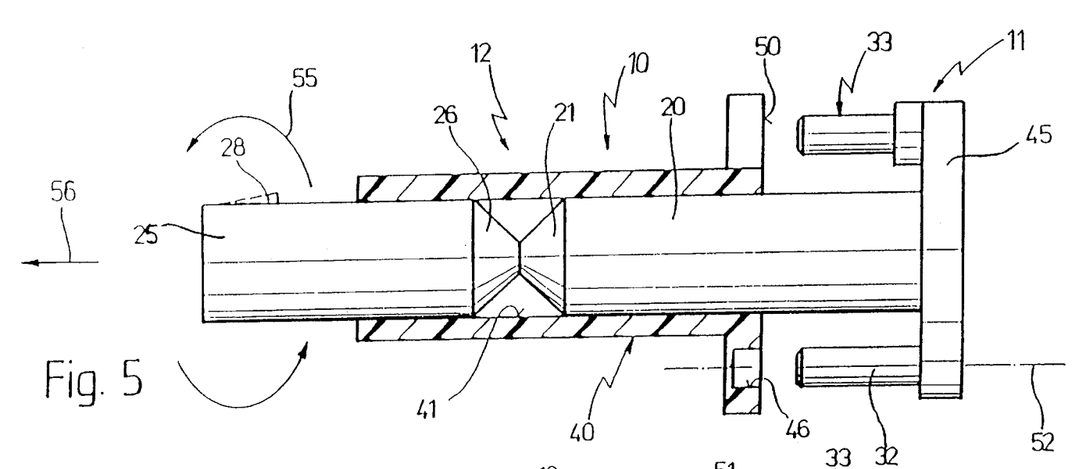
FIG. 5 is a side elevational view, partially cut away, a blood sample taking apparatus with the lancet portion and the sleeve portion mounted within each other prior to the ready-for-use situation of the apparatus.

FIG. 5 shows the result of this unloading, handling and assembling.

As one can see, portions 11 and 12 are so mounted together that pins 32 and 33 are directed towards surface 25 of annular flange 45. Second cylindrical section 25 protrudes over the opposite end of hollow-cylindrical section 40.

In this position the user of blood sample taking apparatus 10 may grasp annular flange 45 with one hand and may grasp the protruding end of second cylindrical section 25 with the other hand. If these two elements are twisted relative to each other, as indicated by an arrow 55 in FIG. 5, second cylindrical section 25 will be separated from first cylindrical section 20 in the direction of arrow 55. The separation may be executed quite easily due to the very thin bridge of material between tips 21, 26. In such a way cutting edge section 24 having been embedded in second cylindrical section 25 and, hence, having been kept sterile, is now exposed.

The user of blood sample taking apparatus 10 may now rotate lancet portion 11 relative to sleeve portion 12 until one of the pins, for example pin 32 is flush with blind bore 46, as indicated by a common axis 52 in FIG. 5. The selection which one of the two pins 32 or 33 shall be brought into alignment with blind bore 46 is facilitated for the user by means of the already mentioned marks 38 on the top side of knob portion 20. Marks 38 may have arbitrary forms, shapes or colours and may cooperate with corresponding countermarks on annular flange 45 which may be applied, for example, on the periphery in a radial extension of the position of blind bore 46.

Parts 11 and 12 are now pushed together by the user in an axial direction such that, as shown in FIG. 6, first pin 32 with its free end enters into blind bore 46 and comes to rest with its tip 36 on bottom 48.

As can clearly be seen from FIG. 6, the now exposed cutting edge section 24 is located within hollow-cylindrical section 40 in a distance from a bottom edge 58 of hollow-cylindrical section 40, being opposite annular flange 45. In this configuration apparatus 10 may be applied to a skin surface of the patient, for example on a finger tip, as indicated in FIG. 6 by reference numeral 59.

The user of the apparatus now grasps hollow-cylindrical section 40 at the bottom side 51 of annular flange 45, for example by his index finger and middle finger and presses his thumb on the top side of knob portion 30 as indicated in FIG. 6 by an arrow 60. By appropriately shaping bottom side 51, one may ensure that the user's fingers are not located below bottom 48.

If the axial force between the fingers (arrow 60) is now increased, first pin 32 will eventually perforate bottom 48 of blind bore 46, such that lancet portion 11 shoots to the left hand side in FIG. 6 such that cutting edge section 24 travels past bottom edge 58.

Figure 7:
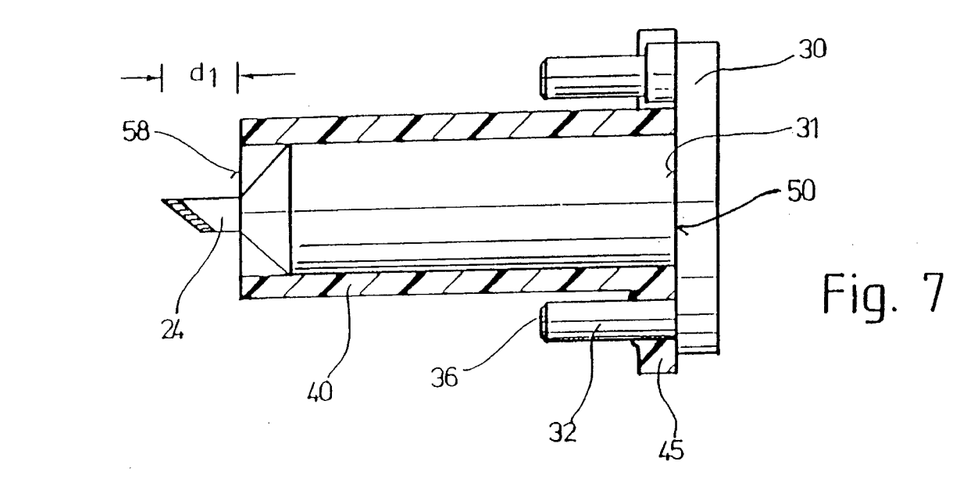
FIG. 7 is an illustration similar to that of FIG. 6, however, in a second operational position of the apparatus.

The final position is shown in FIG. 7. As one can see, first pin 32 has perforated bottom 48 and knob portion 30 rests with its bottom side 31 on top side 50 of annular flange 45.

The design, i.e. the dimensioning of the various axial lengths is made such that cutting edge section 24 in the final position of FIG. 7 projects by a predetermined amount $d_1$ over bottom edge 58 of hollow-cylindrical section 40. The amount $d_1$ corresponds to the intrusion depth.

Figure 8:
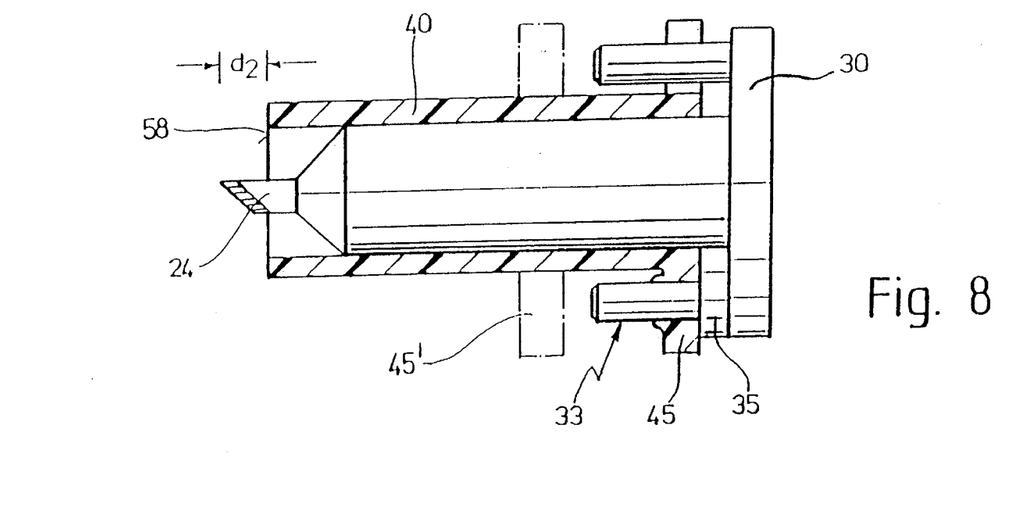
FIG. 8 is an illustration similar to that of FIG. 7, however, with a modified setting of the apparatus for a reduced intrusion depth.

If, however, a position similar to that of FIG. 6 is set in such a way that instead of first pin 32 second pin 33 comes into engagement with blind bore 46, a final position after the perforation of bottom 48 will be achieved as shown in FIG. 8 where knob portion 30 and annular flange 45 are still axially separated from each other by a distance corresponding to the axial dimension of bulged section 35 on second pin 33.

In this case the intrusion depth is reduced to amount $d_2$.

Therefore, by rotating lancet portion 11 relative to sleeve portion 12 the intrusion depth may be set differently to be $d_1$ or $d_2$ by appropriately bringing into mutual engagement either first pin 32 or second pin 33 with blind bore 46. This is indicated by marks 38 being, for example, designed as arrows of different lengths.

It goes without saying that instead of two pins 32 and 33 also three or more pins might be provided, for achieving a more differentiated stepping of intrusion depths.

A first variant of the afore-described embodiment is indicated by reference numeral 36' in FIG. 4a showing that the axial length of the pins may be designed differently. The amount of intrusion depths $d_1$ and $d_2$, respectively, in FIG. 7 and FIG. 8, respectively, is independent of the axial length of pins 32 and 33, respectively. However, a longer pin 32 or 33 has a longer "run-up" between the first operational position according to FIGS. 7 and 8, respectively. The impact of the impinging of the two parts 11, 12 on each other is, therefore, correspondingly bigger with correspondingly longer pins. Therefore, one may set correspondingly greater or smaller forces of impingement for a softer or a harder skin.

Further, FIG. 8 shows still another embodiment of the invention having an auxiliary flange 45' molded on hollow-cylindrical section 40 distant from annular flange 45 in order to be better able to grasp the apparatus while avoiding that the user's fingers come in contact with pins 33 shooting in a forward direction.

Figure 3A:
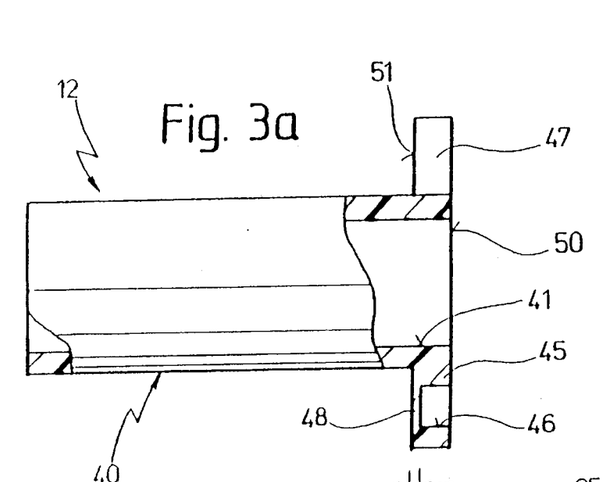
FIGS. 3a and 3b are side elevational views, partially cut away, and a front end view of the sleeve section according to FIG. 2.
Figure 3B:
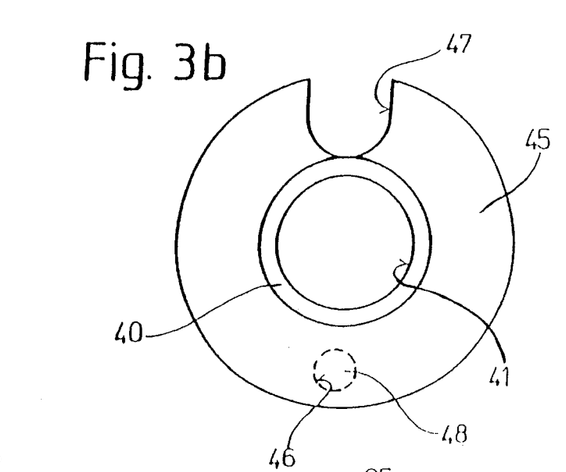
Figure 9:
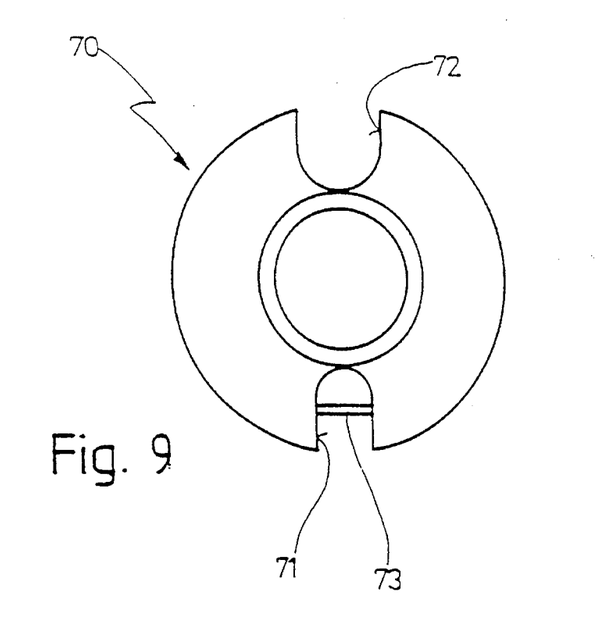
FIG. 9 is a front elevational view, similar to that of FIG. 3b of a knob portion, according to another embodiment of the invention.

FIG. 9 in an illustration similar to that of FIG. 3b shows another design alternative for a preset breaking point.

For that purpose a knob portion 70 is provided with a first cutout 71 at the position where blind bore 46 was in bottom 48 in the embodiment described before. Cutout 71 is arranged diametrically opposite to a second cutout 72. Second cutout 72 can be designed such as cutout 47 in the afore-described embodiment.

First cutout 71 is provided with a thin web 73, for example on that side of knob portion 70 opposite to the viewer of FIG. 9 or on half the height of first cutout 71.

Web 73 with its width and depth is dimensioned such that it again acts as a preset breaking point, similar to bottom 48 in blind bore 46 with the afore-described embodiments.

For breaking through or shearing off web 73 a corresponding protrusion or nose must be provided on the lancet portion (not shown), which is usefully guided through first cutout 71.

Figure 10:
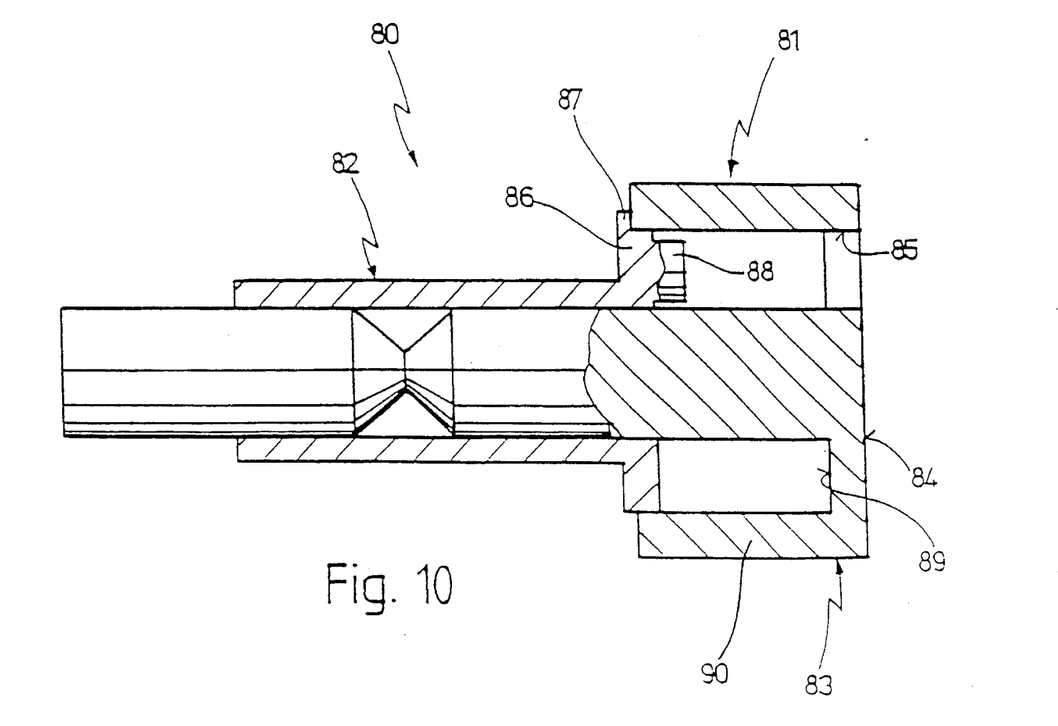
FIG. 10 is an illustration, similar to that of FIG. 6, however, for another embodiment of the invention.

FIG. 10 shows another embodiment of the invention in an illustration similar to that of FIG. 6.

According to this embodiment a blood sample taking apparatus 80 again is provided with a lancet portion 81 and a sleeve portion 82. A knob portion 83 is molded to lancet portion 81 at its right hand terminal end in FIG. 10, however, knob portion 83 in this case is designed in a cap-like manner.

A bore 85 is provided in a top surface 84 of knob portion 83 at an upper peripheral position in FIG. 10.

Knob portion 83 in a cap-like fashion encloses an annular flange 86 of sleeve portion 82. In the upper peripheral position of FIG. 10 annular flange 86 is provided with a protruding nose 87 on which knob portion 83 comes to rest in an axial direction.

Nose 87 in this case acts as a preset breaking point because it may be sheared off by a wall 90 of cap-like knob 83 when lancet portion 81 is pushed against sleeve portion 82 in axial direction.

In order to provide for different intrusion depths in that case a pin 88 may be provided on a top side of annular flange 86. The diameter of pin 88 is smaller than that of bore 85.

In the position shown in FIG. 10 lancet portion 81 will travel the full intrusion distance as compared with sleeve portion 82 because pin 88 will pass through bore 85 in the pushed-together state.

If, however, for setting a smaller intrusion depth sleeve portion 82 is rotated from its position shown in FIG. 10 by 180 degrees so that bore 85 is now in the lower position, then pin 88 will impinge on an inner surface 89 of knob portion 83 so that intrusion depth will be reduced by the axial length of pin 88.

The embodiments of FIGS. 9 and 10 show that the present breaking point according to the present invention may be designed in many different ways without departing from the scope of the present invention.

What is claimed is:

1. An apparatus for taking blood samples comprising:

an elongate lancet portion defining an axis and having a first and a second terminal end, said first lancet portion terminal end being provided with a knob section and said second lancet portion terminal end being provided with a protruding lancet cutting edge section;

an elongate sleeve portion for receiving and axially guiding said lancet portion, said sleeve portion having a first and a second terminal end, said first sleeve portion terminal end being provided with a flange; and present breaking point means, wherein said lancet portion, in a first operational position, is axially held within said sleeve portion with said knob section being at a first axial distance from said flange and said protruding lancet cutting edge section being entirely enclosed by said second sleeve portion terminal end, whereas, in a second operational position, said lancet portion is axially held within said sleeve portion with said knob section being at a second axial distance from said flange and said protruding lancet cutting edge section protruding from said second sleeve portion terminal end, said present breaking point means acting, in an unbroken state, as axial stop means between said lancet portion and said sleeve portion, whereas upon application of a predetermined amount of axial force between said lancet portion and said sleeve portion said present breaking force means is broken, resulting in an abrupt transition from said first to said second operational position.

2. The apparatus of claim 1, wherein said present breaking point means is designed as a perforatable bottom section on said sleeve portion, a pin being provided on said lancet portion, said pin registering with said bottom section and punching through said bottom section during said transition.

3. The apparatus of claim 1, wherein said preset breaking point means is designed as a web on said sleeve portion, a protrusion being provided on said lancet portion, said protrusion registering with said web and shearing off said web during said transition.

4. The apparatus of claim 1, wherein said preset breaking point means is designed as a nose on said sleeve portion, a protrusion being provided on said lancet portion, said protrusion registering with said nose and shearing off said nose during said transition.

5. The apparatus of claim 1, wherein said lancet portion and said sleeve portion are made of a plastic material.

6. An apparatus for taking blood samples, comprising:

an elongate lancet portion defining an axis and having a first and a second terminal end, said first lancet portion terminal and being provided with a knob section and said second lancet portion terminal end being provided with a protruding lancet cutting edge section;

an elongate sleeve portion for receiving and axially guiding said lancet portion, said sleeve portion having a first and a second terminal end, said first sleeve portion terminal end being provided with a flange;

at least two spacer means arranged between said lancet portion and said sleeve portion for establishing either a first or a second axial distance therebetween; and mechanical axial obstacle means arranged between said lancet portion and said sleeve portion, said mechanical axial obstacle means being adapted to be overcome upon application of a predetermined amount of axial force between said lancet portion and said sleeve portion, wherein said lancet portion, in a first operational position, is axially held within said sleeve portion with said knob section being at said first or said second axial distance, respectively, from said flange and said protruding lancet cutting edge section being entirely enclosed by said second sleeve portion terminal end, whereas, in a second operational position, said lancet portion is axially held within said sleeve portion with said knob section being at a third axial distance from said flange and said protruding lancet cutting edge section protruding from said second sleeve portion terminal end, said mechanical axial obstacle means acting with said first or said second spacer means, respectively, as axial stop means between said lancet portion and said sleeve portion, whereas upon application of said predetermined amount of axial force between said lancet portion and said sleeve portion, said mechanical axial obstacle means is overcome, resulting in an abrupt transition from said first to said second operational position.

7. The apparatus of claim 6, wherein said spacer means are designed as axial pins.

8. The apparatus of claim 7, wherein said pins, during said transition, run in a bore, at least one of said pins being provided with a bulged section having a larger diameter than said bore.

9. The apparatus of claim 7, wherein said pins are provided on said knob portion, said flange having throughs registering with said pins.

10. The apparatus of claim 7, wherein said pins have a different axial length.

11. The apparatus of claim 7, wherein at least one of said pins has stepped diameters.

12. The apparatus of claim 6, wherein said mechanical axial obstacle means is designed as a present breaking point means.

13. An apparatus for taking blood samples, comprising:

an elongate lancet portion defining an axis and having a first and a second terminal end, said first lancet portion terminal end being provided with a knob section and said second lancet portion terminal end being provided with a protruding lancet cutting edge section;

an elongate sleeve portion for receiving an axially guiding said lancet portion, said sleeve portion having a first and a second terminal end, said first sleeve portion terminal end being provided with a flange;

protection means arranged on said lancet portion and enclosing said protruding lancet cutting edge section, said protection means being adapted to be manually removed from said lancet portion to expose said protruding lancet cutting edge section, said protection means having a barb means disposed thereon; and mechanical axial obstacle means arranged between said lancet portion and said sleeve portion, said mechanical axial obstacle means being adapted to be overcome upon application of a predetermined amount of axial force between said lancet portion and said sleeve portion, wherein said lancet portion, in a first operational position, is axially held within said sleeve portion with said knob section being at a first axial distance from said flange and said protruding lancet cutting edge section being entirely enclosed by said second sleeve portion terminal end, said protection means protruding, however, from said second sleeve portion terminal end for being removed from said lancet cutting edge in said first operational positions, whereas, in a second operational position, said lance portion is axially held within said sleeve portion with said knob section being at a second axial distance from said flange and said protruding lancet cutting edge section protruding from said second sleeve portion terminal end, said mechanical obstacle means acting as axial stop means between said lancet portion and said sleeve portion, whereas upon application of said predetermined amount of axial force between said lancet portion and said sleeve portion, said mechanical axial obstacle means is overcome, resulting in an abrupt transition from said first to said second operation position.

14. The apparatus of claim 13, wherein said lancet portion comprises a first cylindrical section for supporting a lancet shank section, said protection means comprising a second cylindrical section being essentially flush with said first cylindrical section.

15. The apparatus of claim 13, wherein said first and said second cylindrical sections are integrally made from plastic material.

16. The apparatus of claim 14, wherein at least one of said cylindrical sections is provided with a tip, said tip being adapted to form a structural transition to the other one of said first cylindrical sections.

\* \* \* \* \*